(12) United States Patent  
Kuramori et al.

(10) Patent No.: US 7,467,010 B2
(45) Date of Patent: Dec. 16, 2008

(54) STRESS-AT-WORK EVALUATING DEVICE AND METHOD

(75) Inventors: Akira Kuramori, Kanagawa (JP);
Noritaka Koguchi, Kanagawa (JP);
Masayoshi Kamijo, Nagano (JP);
Tsugutake Sadoyama, Ibaraki (JP)

(73) Assignee: Yokohama Rubber Co., Ltd., Tokyo (JP)

( * ) Notice: Subject to any disclaimer, the term of this patent is extended or adjusted under 35 U.S.C. 154(b) by 427 days.

(21) Appl. No.: 10/942,041

(22) Filed: Sep. 16, 2004

(65) Prior Publication Data

US 2005/0090757 A1 Apr. 28, 2005

(30) Foreign Application Priority Data

Sep. 17, 2003 (JP) ............... 2003-325043

(51) Int. Cl.
*A61B 5/04* (2006.01)
(52) U.S. Cl. .................................... 600/546
(58) Field of Classification Search ................. 600/546
See application file for complete search history.

(56) References Cited

U.S. PATENT DOCUMENTS 4,344,441 A * 8/1982 Radke ................... 600/546
4,934,378 A * 6/1990 Perry, Jr. ................. 600/546

FOREIGN PATENT DOCUMENTS

EP 1 535 570 A1 6/2005

JP 11-019075 1/1999
JP 2002230699 A * 8/2002
JP 2004-049623 2/2004

OTHER PUBLICATIONS

Siegmund, Gunter P. et al., Startle Response of Human Neck Muscles Sculpted By Readiness to Perform Ballistic Head Movements, 2001 The Journal of Physiology 535:289-300.*

Lehman, Gregory J. et al., The Importance of Normalization in the Interpretation of Surface Electromyography: A Proof of Principle, Sep. 1999 The Journal of Manipulative and Physiological Therapeutics vol. 22 No. 7 pp. 444-446.*

Healey, J.A., "*Wearable and Automotive Systems for Affect Recognition from Physiology,*" Massachusetts Institute of Technology, pp. 41-158 (May 2000), XP-002318020.

(Continued)

*Primary Examiner*—Max Hindenburg
*Assistant Examiner*—Emily M Lloyd
(74) *Attorney, Agent, or Firm*—Finnegan, Henderson, Farabow, Garrett, Dunner, LLP.

(57) ABSTRACT

A stress-at-work evaluating device evaluates a stress of a subject at work by measuring activities of one of the right and the left masseter muscles, the work including exercise of arms or feet of the subject. The device evaluates the stress from a normalized intensity of the myoelectric potential one of the right and the left masseter muscles. The normalized intensity is calculated by dividing the intensity of the measured myoelectric potential of the masseter muscles by the level of the external force acting on the head of the subject at work.

8 Claims, 10 Drawing Sheets

OTHER PUBLICATIONS

Veiersted, K.B., et al., "*Electromyographic evaluation of muscular work pattern as a predictor of trapezius myalgia*," Scand. J. Work Environ. Health, vol. 19, pp. 284-290 (1993), XP-008042958.
Abstract of Japan, JP2002230699, (Dec. 12, 2002) (1 page).
Helander, M., "*Applicability of Drivers' Electrodermal Response to the Design of the Traffic Environment*," Journal of Applied Psychology, vol. 63, No. 4, pp. 481-488 (1978), XP008042846.
Healey, J., et al., "*SmartCar: Detecting Driver Stress*," Pattern Recognition, Proceedings 15th International Conf., Los Alamitos, California (Sep. 3-7, 2000), vol. 4, pp. 218-221, XP010533059.
Picard, R.W., "*Toward Machine Emotional Intelligence: Analysis of Affective Physiological State*," IEEE Transactions on Pattern Analysis and Machine Intelligence, New York, vol. 23, No. 10, pp. 1175-1191 (Oct. 2001), XP002268746.

* cited by examiner

NORMALIZED MYOELECTRIC POTENTIAL
INTENSITY OF DRIVER D1

NORMALIZED MYOELECTRIC POTENTIAL
INTENSITY OF DRIVER D2

STRESS-AT-WORK EVALUATING DEVICE AND METHOD

BACKGROUND OF THE INVENTION

The present invention relates to a stress-at-work evaluating device and a stress-at-work evaluating method, and more particularly to a device for evaluating a stress of a subject at work.

A method using biological information, such as an electromyogram (EMG) or a brain wave, is known as a general technique for measuring the mental burden (stress) of a subject. The method using biological information frequently imparts some restriction on a subject and needs a relatively long recording time to analyze the acquired data. For this reason, the method cannot be used for evaluating the mental stress of a subject if the subject is not confined to bed (for example, JP 11-19075 A).

A person frequently suffers from great mental stress when he/she drives a vehicle (stress while working). The level of stress varies from person to person, and situations where the person suffers from stress vary from person to person. In a situation where riding in a vehicle is uncomfortable or controllability (steering performance) of the vehicle is poor, excessive strain is apt to occur in the driver. Such excess strain is likely to interfere with smooth driving, possibly causing an accident.

During the development and design of a vehicle etc., an electromyogram, which is easily measured and used, is obtained from myoelectric signals. These myoelectric signals show activities of muscles in parts of the human body, those muscles being heavily loaded during driving. By detecting myoelectric signals of muscles heavily burdened (i.e., muscles of the arms and feet), the mental stress of the subject driving the vehicle is directly evaluated.

When a human being suffers from mental stress, the muscle sustains excessive strain due to unintentional muscle activity. Accordingly, such mental stress can be measured by measuring the muscle's activity.

Activities of the arms and the feet, which are largely exercised in work such as driving a vehicle, are acquired in the form of an electromyogram (EMG), whereby activity of the muscles at work is measured and stress on the human body is judged in conventional cases. However, a method of objectively expressing a person's mental burden (mental stress) while working using an EMG has not been found yet.

In an EMG representing the activities of the muscles at work such as the arm and the foot, a myoelectric signal indicating the muscle activities brought on by work such as driving a vehicle and a myoelectric signal representing the "excessive muscle strain" caused by stress are superposed on each other. It is thus difficult to discriminate the muscle activity due to driving from the muscle activity due to mental stress.

Methods using biological information other than an EMG often impart some restriction on a subject and need a relatively long recording time to analyze the acquired data. Therefore, it is difficult to correctly evaluate mental stress at work.

During conventional development and design of a vehicle etc., items relating to a driver's mental burden (mental stress), such as riding comfort and controllability (steering performance), are merely described subjectively in terms of the driver's opinion about driving the vehicle. As a result, it is impossible to objectively judge mental stress in the driver while driving.

SUMMARY OF THE INVENTION

The present invention has been made in view of the above, and has an object to provide a stress-at-work evaluating device which objectively judges a subject's mental stress when he/she engages in work such as driving. The device quantitatively measures the "excessive muscle strain," resulting from the stress, that is generated in the masseter muscles of the subject. The invention also provides a stress-at-work evaluating method.

In order to attain the object described above, the present invention provides a stress-at-work evaluating device for evaluating a subject's stress at work based on measurement of activities of one of the right and the left masseter muscles, the work including exercising the arms or feet of the subject, wherein the stress-at-work evaluating device comprises: a sensor unit for sensing a myoelectric potential of one of the right and the left masseter muscles, the potential being generated through the activities of the one of the masseter muscles at work; an amplifier for amplifying the myoelectric potential sensed by the sensor unit; a myoelectric-potential data processing part for processing time-series data of the amplified myoelectric potential of the one of the right and the left masseter muscles, to thereby calculate intensity of the myoelectric potential of the one of the right and the left masseter muscles; an external-force level judging part for judging a level of an external force acting on a portion of the head of the subject at work, the external force measured simultaneously with the myoelectric potential; and an evaluating part for evaluating the level of stress of said subject at work, the level of stress obtained by normalizing the calculated intensity of the myoelectric potential by the judged level of the external force.

Preferably, the external-force level judging part judges the level of the external force acting on a portion of the head of the subject from the intensity of the myoelectric potential of at least one of muscles which holds the posture of the head.

Also preferably, the work entails moving a predetermined object by operation of the subject, to thereby cause the external force acting on a portion of the head of the subject. The external-force level judging part judges the level of the external force acting on the portion of the head by using at least one of physical quantities representing the movement of the object which is caused by the work. The work is, for example, a steering operation which is done by the subject.

Preferably, the evaluating part evaluates the level of stress of the subject at work by comparing the normalized intensity of the myoelectric potential with predetermined values.

The invention also provides a stress-at-work evaluating method for evaluating the stress of a subject at work based on the measurement of activities of one of the right and left masseter muscles, the work including exercise of arms or feet of the subject, wherein the stress-at-work evaluating method comprises: a myoelectric potential measurement step of sensing and amplifying a myoelectric potential of one of the right and the left masseter muscles, the potential being generated through the activities of the one of the right and left masseter muscles at work; a processing step of processing time-series data of the measured myoelectric potential of the one of the right and the left masseter muscles and calculating intensity information on the myoelectric potential of the one of the right and the left masseter muscles; a judging step of judging a level of an external force acting on the head of the subject at work, the external force measured simultaneously with the myoelectric potential; and an evaluating step of evaluating the level of stress of the subject at work, the level of stress obtained by normalizing the calculated intensity of the myoelectric potential by the judged level of the external force level.

According to the present invention, the stress of a subject at objective work can be evaluated based on measurement of the activities of one of the right and the left masseter muscles, from the myoelectric potential of one of the right and the left masseter muscles when the subject is working. The work includes exercise of the arms or feet of the subject.

Therefore, according to the present invention, the mental stress of a subject while steering a vehicle can be objectively evaluated by quantitatively expressing information related to mental stress, such as riding comfort and controllability (steering performance), in the subject when the subject steers the vehicle.

This application claims priority to Japanese patent application No. 2003-325043, the entire contents of which are hereby incorporated by reference herein.

DESCRIPTION OF THE PREFERRED INVENTION

A stress-at-work evaluating device and a stress-at-work evaluating method, which are believed to be the best modes of the present invention, will be described with reference to the accompanying drawings.

Figure 1:
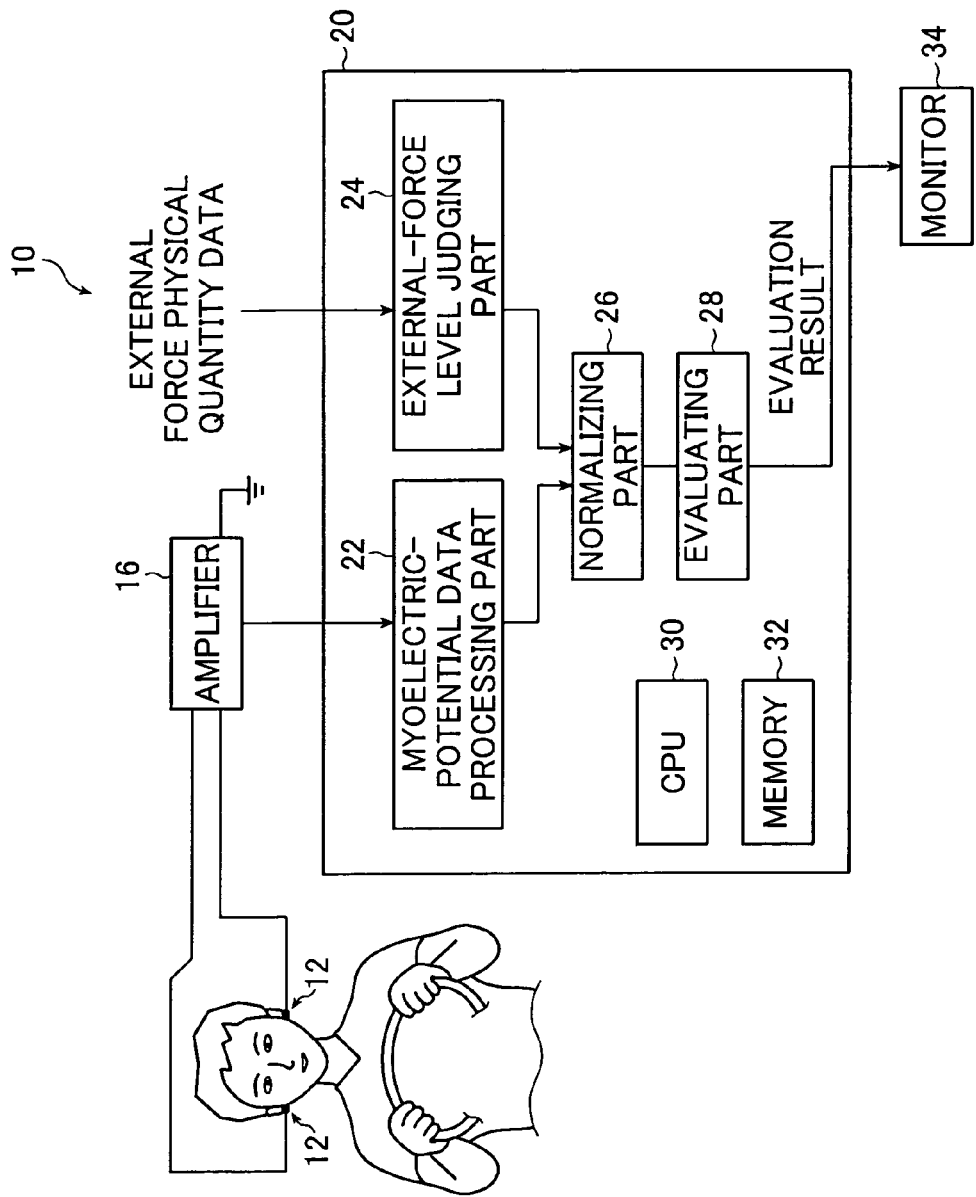
FIG. 1 is a diagram, in block and schematic form, showing a steering stress evaluating device 10, which is an embodiment of the present invention.

FIG. 1 is a diagram, in block and schematic form, showing a steering stress evaluating device 10 (referred to as an evaluating device 10) in which the stress-at-work evaluating device of the present invention is used during steering operation done by a driver as a subject. FIG. 1 also shows an evaluating device 10 of the later explained third embodiment of the present invention.

The evaluating device 10 evaluates the mental stress of a driver while driving a vehicle when he/she steers the vehicle. The evaluating device is made up of one or more sensor units 12 for detecting the time-series myoelectric potential or potentials of one or both of the right and the left masseter muscles of the driver, an amplifier 16 for amplifying the myoelectric potential or potentials detected by one or more sensor units 12, and a processor unit 20 for evaluating the mental stress of the driver, when he/she steers the vehicle, by using the time-series data of the amplified myoelectric potential or potentials of one or both of the masseter muscles, and the level of an external force acting on the head of the driver.

When external force is applied to the head of a worker (subject) who is doing objective work, the muscles that support the head of the worker contract to hold his head's posture. The level of the external force corresponds to a level of a force to hold the posture of the worker. The level can be judged by using the myoelectric potential of the above mentioned head supporting muscle, the myoelectric potential generated simultaneously.

During objective work, for example a steering operation of a vehicle, a subject operates the object to move an object. When this movement causes an external force to act on the head of the worker at work, the level of the external force can be judged by using a physical quantity featuring the movement of the object (e.g., vehicle) (The evaluation for the level of the external force will be described in detail later.).

Figure 2:
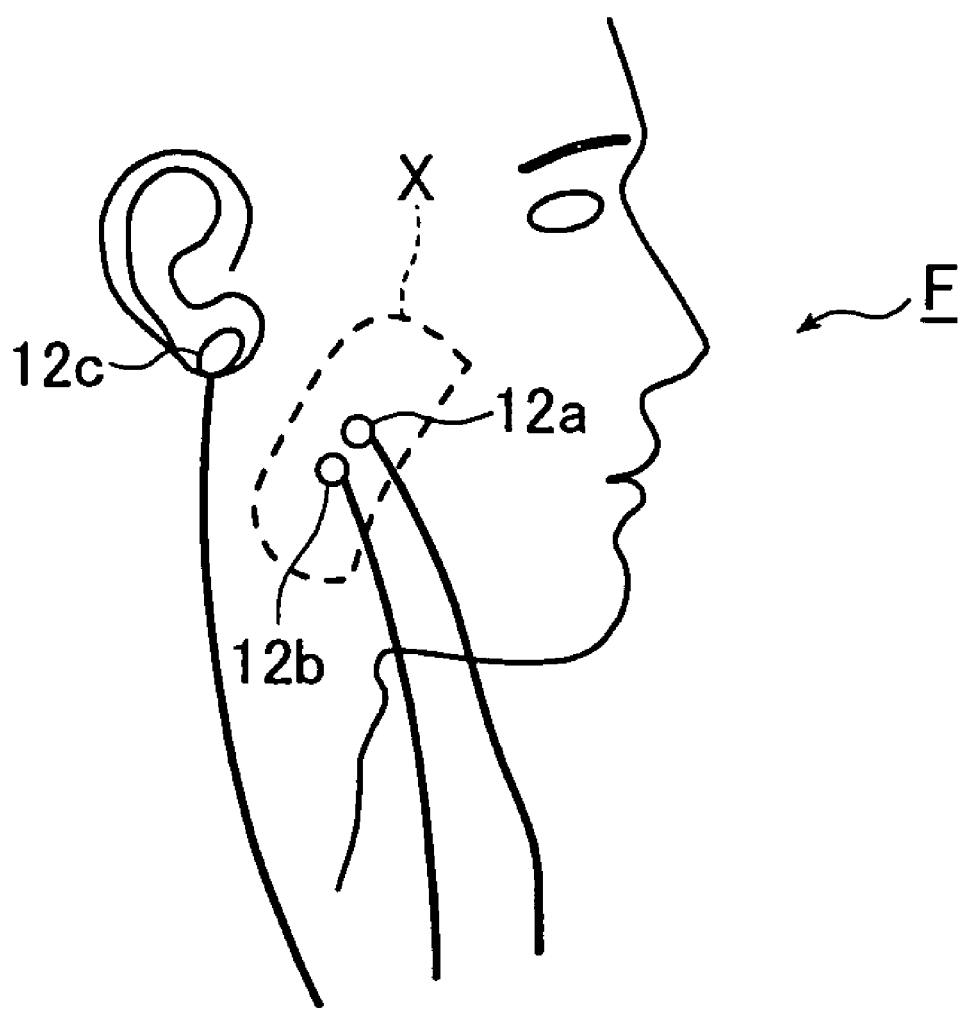
FIG. 2 is a diagram for explaining how to attach a sensor unit 12 of the steering stress evaluating device 10 shown in FIG. 1 to a driver.

The sensor units 12 detect a myoelectric potential or potentials of one or both of the right and left masseter muscles of the driver. FIG. 2 is a diagram for explaining how to attach the sensor unit 12 to a driver. Each of the sensor units 12 includes a couple of electrodes 12a and 12b, which are attached while being spaced away from each other by about 5 mm, and an earth electrode 12c for a reference potential. As shown in FIG. 2, the electrodes 12a and 12b are stuck to the skin covering an upper part of a masseter muscle X (enclosed by a broken line) of a face F. The ground electrode 12c is stuck to an earlobe. Those electrodes 12a, 12b, and 12c may be Ag/AgCl dish-like electrodes, Ag electrodes, or stainless electrodes.

Before the electrodes are stuck onto the skin surface of the driver, each electrode is scrubbed with a suitable means, and cleaned by using alcohol, and then is attached to the skin surface by using electrode paste. In this case, the cleaning operation is continued until electric resistance of each electrode is reduced to 30 k$\Omega$ (preferably 5 k$\Omega$). The paired electrodes are attached onto a venter of the muscle such that those electrodes are arranged in parallel with the muscular fiber.

The electrode 12c is a ground electrode to be attached to an earlobe of the driver, which is an electrically inactive position, in order to hold the potential of the driver constant. Use of the ground electrode ensures an exact measurement carried out by the potential electrodes 12a and 12b. In FIG. 2, the sensor unit 12 is stuck so as to measure a myoelectric potential of the right masseter muscle. When the myoelectric potential of the left masseter muscle is measured, the sensor unit is stuck as in the right masseter case.

The ground electrode 12c connected to the amplifier 16 is grounded through the amplifier 16. The amplifier 16 is a known amplifier for amplifying a myoelectric potential or potentials detected by one or more sensor units 12.

The masseter muscles are large muscles located on the sides of the face. The masseter muscles and the temporalis muscle are both called mastication muscles. The masseter muscles act to close the jaw of the subject, for example, to masticate and speak. Accordingly, the masseter muscles do not act during driving work, which is normally done using the muscles of the arms and the feet. When stress is placed on the subject, the subject unconsciously performs "teeth clenching" as the result of stress generation. Accordingly, the masseter muscles activate. The evaluating device 10 evaluates the level of mental stress of the driver by measuring the myoelectric potential or potentials of one or both of the masseter muscles and evaluating the "teeth clenching" intensity of the driver.

The processor unit 20 contains a myoelectric-potential data processing part 22, an external-force level judging part 24, a normalizing part 26, an evaluating part 28, a CPU 30, a memory 32, and a monitor 34. The myoelectric-potential data processing part 22 processes, as designed, time-series data of the myoelectric potential or potentials of output of one or both of masseter muscles from the amplifier 16 to thereby generate one or more waveforms (referred to as one or more myoelectric potential waveforms), smoothly shaped, of the myoelectric potential of one or both of masseter muscles. Then, the myoelectric-potential data processing part 22 calculates from one or more myoelectric potential waveforms a myoelectric potential intensity (the myoelectric potential intensity will be described in detail later) to produce intensity information on the myoelectric potential of one or both of masseter muscles in a predetermined time region. The external-force level judging part 24 evaluates the level of an external force acting on the head of the subject during the objective work, from external force physical quantity data. The external force physical quantity data indicates the level of external force acting on the head of a worker already separately measured. The normalizing part 26 normalizes the calculated myoelectric potential intensity by the judged external force level. The evaluating part 28 evaluates a level of stress at work by using the normalized myoelectric potential intensity. The CPU 30 controls and manages operations of the respective parts. The memory 32 stores data obtained in the respective parts and calculation results. The monitor 34 displays the processing results output from the related parts and the evaluation results. The external force physical quantity will subsequently be described in detail.

The processor unit 20 may be prepared using a hardware arrangement in which the respective parts of the unit are circuitries so designed as to have related functions, or a software arrangement configured to exercise the functions of the related parts by programs on a computer.

In a first embodiment of a method of evaluating a mental stress of a driver when he/she steers a vehicle, which will be described later, the myoelectric-potential data processing part 22 samples the time-series data of the myoelectric potential of one of the right and left masseter muscles during the objective work, performs full-wave rectification on the sampled data, smoothes the rectified one to thereby generate a myoelectric potential waveform, and finally calculates a myoelectric potential intensity from this myoelectric potential waveform in a predetermined time region for output.

The "myoelectric potential intensity in a predetermined time region" means, for example, a root mean square (RMS) (effective value) of the myoelectric potential waveform, or an integrated electromyogram (IEMG) thereof, which are calculated in a predetermined time region.

In a second embodiment of the stress evaluating method, which will also be described later, the myoelectric-potential data processing part samples the time-series data of myoelectric potentials of both the right and left masseter muscles during the objective work, performs full-wave rectification on both the sampled data, smoothes the rectified ones to thereby generate smooth myoelectric potential waveforms, calculates a simultaneous contraction waveform in a predetermined time region from the myoelectric potential waveforms of those masseter muscles, and finally calculates a simultaneous contraction intensity from the simultaneous contraction waveform.

The term "simultaneous contraction waveform" is a waveform obtained by calculating a geometric average of the myoelectric potentials of the right and left masseter muscles at the same time point or a waveform generated by selecting a myoelectric potential which is the smaller in value at the same time point among the myoelectric potentials of the right and left masseter muscles.

The external-force level judging part 24 judges a level of an external force applied to the head of the driver during the driving work.

The judgment of the external force level will be described below. In a process of judging the external force level, the external-force level judging part performs full-wave rectification on time-series data of an acceleration having a lateral direction with respect to the vehicle (the acceleration will be referred to as a lateral acceleration, and corresponds to an input external force physical quantity (which will be discussed in detail later)). Then, the external-force level judging part smoothes the rectified one to form a smooth waveform (referred to as an external force physical quantity waveform) representing the external force physical quantity (lateral acceleration). The external-force level judging part, thereafter, calculates an external force physical quantity, which is an RMS value (or an integrated value) of the external force physical quantity waveform in a predetermined time region, and sets the external force physical quantity as a level of the external force.

The lateral acceleration as the external force physical quantity is measured by a sensor and an amplifier (not shown) fixed to a console of the vehicle, and acquired data is input to the external-force level judging part 24.

When a vehicle is driven, or in a state where a driver sits on a seat of the vehicle for driving, a driver's body receives a force from the vehicle through the seat and moves together with the vehicle.

During driving, the head of the driver is held at substantially fixed position and angle with respect to the driver's body by exercise of a plurality of muscles (temporalis, sternocleidomastoids, trapezius and masseter muscles, and the like). When the driver turns the steering wheel to change the trajectory of the vehicle, the driver receives an acceleration to his head. At this time, those muscles contract and relax to hold the relative position of the head with respect to the body, that is, the muscles act for holding the posture of the head, so that the head holds its position while resisting an external force.

The "external force physical quantity" is a physical quantity that enables one to indirectly estimate a level of an external force applied to the head. In this embodiment, for the external force physical quantity, the following quantities may be enumerated: a physical quantity featuring a motion of the vehicle, a physical quantity featuring a motion of the driver's body, a physical, quantity featuring a motion of the driver's head, and an activity intensity of the muscles of the driver that act to hold the posture of the head. The acceleration that is in the lateral direction with respect to the vehicle is involved in the external force physical quantity.

Figure 3A:
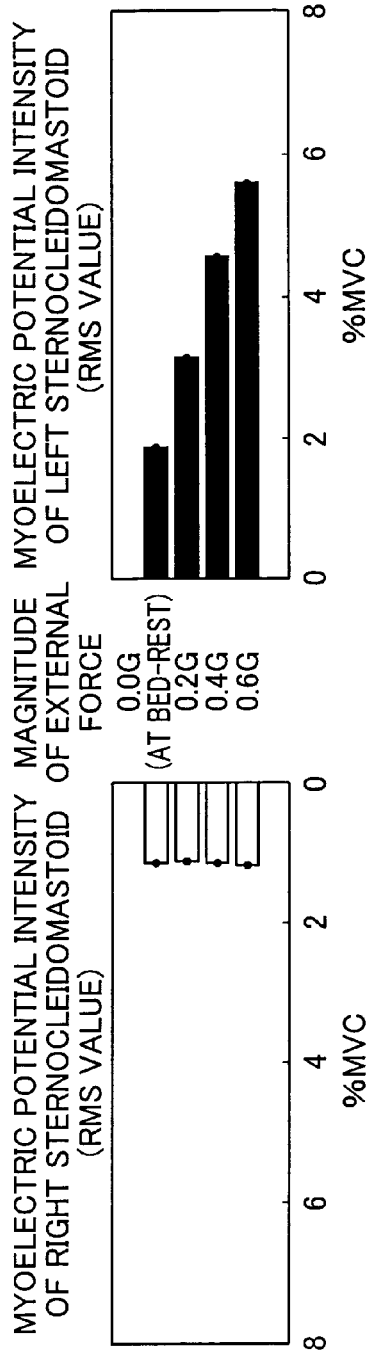
FIGS. 3A and 3B are graphs showing the relationship between an external force laterally applied to the head of a subject and the myoelectric potential intensity of the sternocleidomastoids.
Figure 3B:
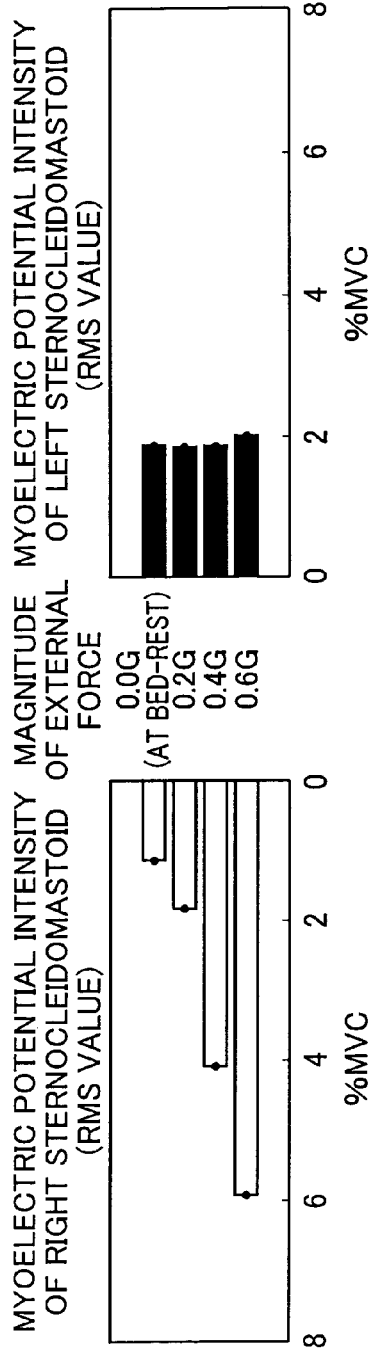

FIGS. 3A and 3B are graphs showing myoelectric potential intensity (RMS values) of the sternocleidomastoids of a subject wearing a helmet when forces are laterally applied to the helmet for a predetermined time. FIG. 3A is a graph showing activities of the right and left sternocleidomastoids when a force is applied to the subject in such a direction to incline his head to the right. FIG. 3B is a graph showing activities of the right and left sternocleidomastoids when a force is applied to the subject to incline his head to the left.

As seen from FIGS. 3A and 3B, as the external force is larger, the myoelectric potential intensity of the muscle located opposite to the side to which the head is inclined, increases. This fact indicates that the sternocleidomastoid located opposite to the side to which the head is inclined contracts so as to stop inclination of the head. That is, the sternocleidomastoid acts to hold the posture of the head while resisting the external force. From this fact, it is confirmed that the myoelectric potential intensity of the sternocleidomastoid, in particular the myoelectric potential intensity of the sternocleidomastoid which is located in the opposite direction to the direction of the applied force to the head, corresponds to the external force acting on the helmet. Therefore, the myoelectric potential intensity of the sternocleidomastoid is found to be the external force physical quantity. In the present invention, the level of the external force acting on the head is represented by using the myoelectric potential intensity of the muscles acting to hold the posture of the head.

In the present invention, the external force physical quantity may be any physical quantity if it enables one to estimate the level of external force applied to the head. For the external force physical quantity, a yaw angle value of the vehicle and a slip angle value, which feature the vehicle motion are additionally enumerated. The steering torque generated when the steering wheel of the vehicle is turned, and the steering operation load as the product of the steering torque and the steering angular velocity are further enumerated for the external force physical quantity. Time-series data of the myoelectric potentials of the masseter muscles, temporalises, sternocleidomastoids and trapezius, and the like, which are the muscles acting for holding the posture of the head of the driver during driving, are also enumerated.

A physical quantity representative of a motion of the driver's head, which is obtained by directly measuring a motion of the driver's head by, for example, motion capture, is also enumerated for the external force physical quantity. There is no special limitation on the external force physical quantity and the judging means for judging the external force level.

The normalizing part 26 normalizes the myoelectric potential intensity that is output from the myoelectric-potential data processing part 22, by dividing the myoelectric potential intensity by the external force physical quantity intensity which is output from the external-force level judging part 24, in which the time region for the external force physical quantity intensity is the same as the time region set for the myoelectric potential intensity when the myoelectric potential intensity is calculated. The normalizing part 26 outputs the normalized myoelectric potential intensity to the evaluating part 28.

The evaluating part 28 evaluates a level of stress placed on a worker at work by, for example, comparing the value of the normalized myoelectric potential intensity with set values of respective stages previously set for stagewise evaluation on levels of stress of the worker at work.

The evaluation result thus obtained, together with one or more myoelectric potential waveforms and the myoelectric potential intensity, is sent to the monitor 34 for display.

A stress-at-work evaluating method carried out in the thus arranged evaluating device 10 will be described in detail by using a method for evaluating stress levels during steering, which is one form of the stress-at-work evaluating method.

Figure 4:
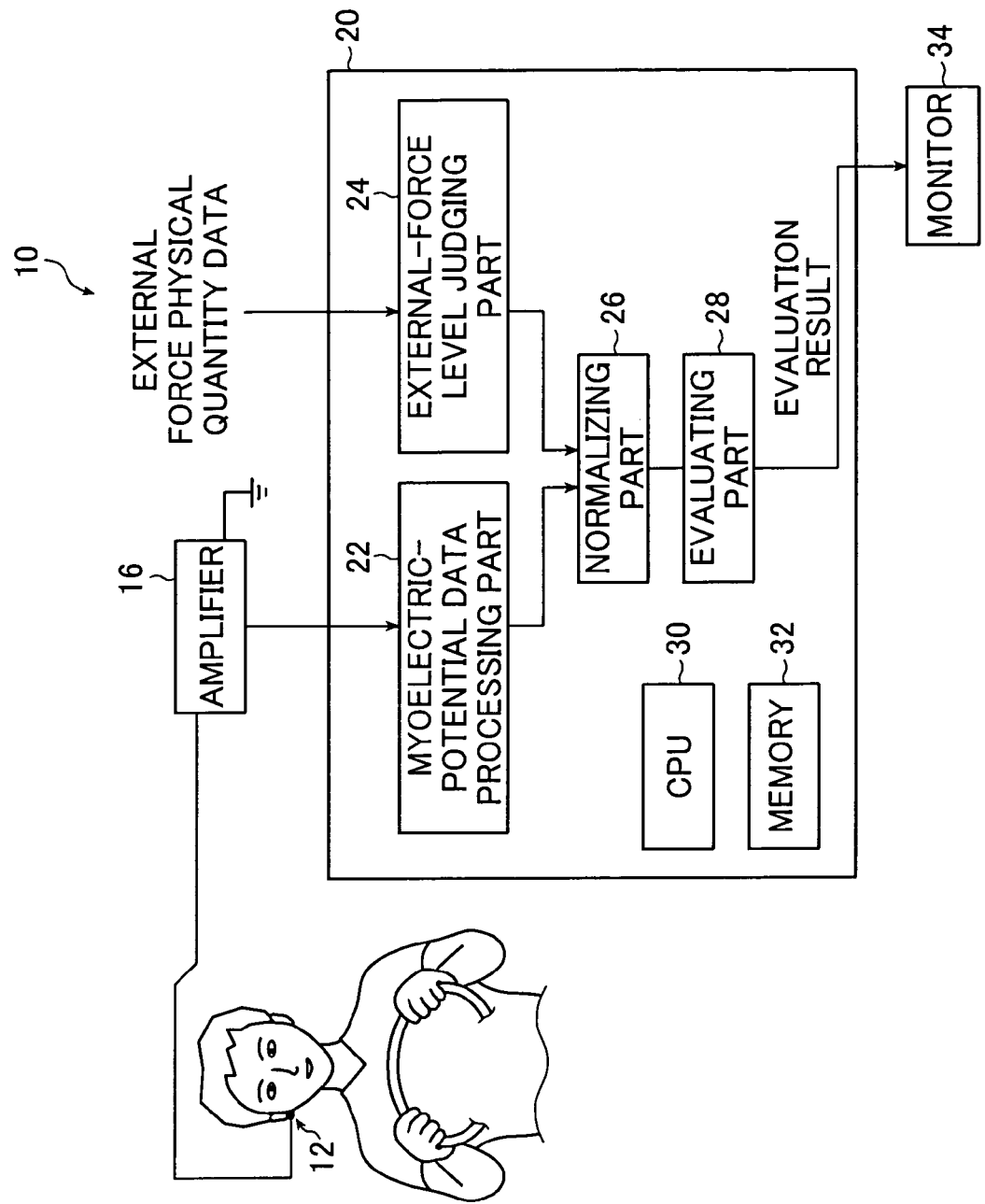
FIG. 4 is a diagram, in block and schematic form, showing a steering stress evaluating device 10 of a first embodiment of the present invention.
Figure 5:
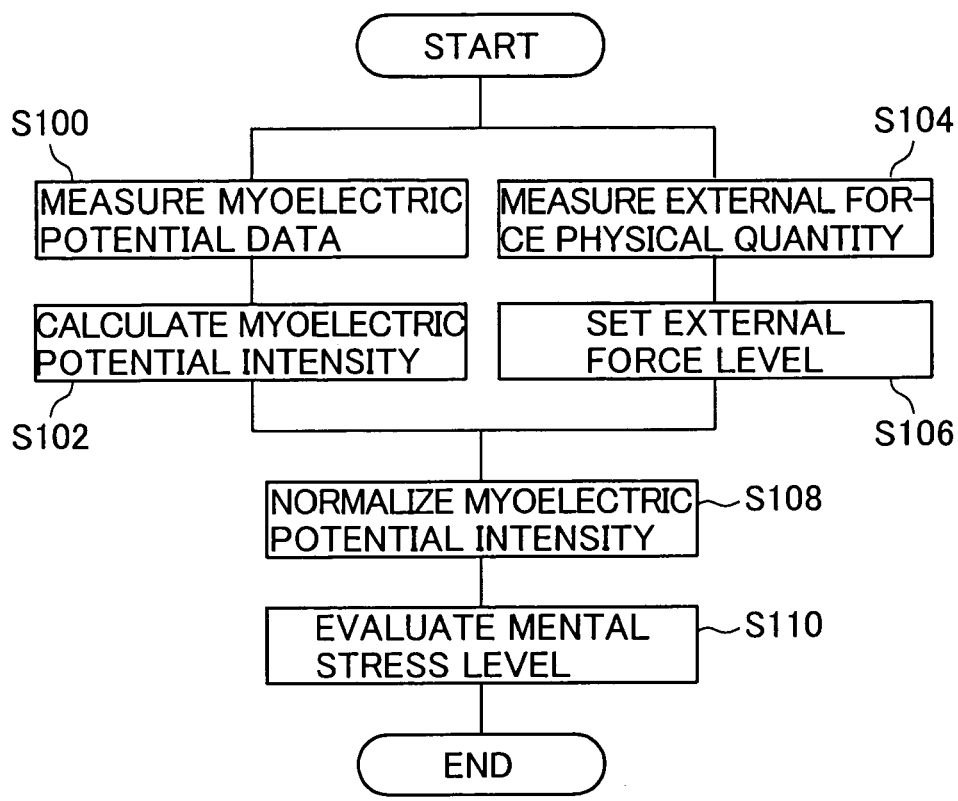
FIG. 5 is a flow chart for explaining a first embodiment of a method for evaluating a mental stress of a driver while steering, which is performed by using the steering stress evaluating device 10.

FIG. 4 is a diagram, in block and schematic form, showing a steering stress evaluating device 10 of a first embodiment of the present invention. FIG. 5 is a flow chart for explaining a first embodiment of a method for evaluating a stress of a driver at steering, which is carried out by using the steering stress evaluating device 10.

In the first embodiment of the stress-at-steering evaluating method, time-series myoelectric potential data of one of the right and left masseter muscles of the driver during steering are acquired by measurement, and the myoelectric potential intensity in a predetermined time region while the vehicle is running is obtained. Also in the evaluating method, time-series lateral acceleration of the vehicle as the external force physical quantity is measured, and the external force physical quantity intensity in a predetermined time region while the vehicle is running is obtained. The first embodiment of the stress-at-steering evaluating method normalizes the myoelectric potential intensity in the predetermined time region by dividing the myoelectric potential intensity by the external force physical quantity in the predetermined time region, and evaluates the stress of the driver when he/she steers the vehicle.

In the first embodiment of the stress-at-work evaluating method described above, as shown in FIGS. 4 and 5, the sensor unit 12 is stuck to a driver as a subject as shown in FIG. 2. The driver starts to drive, steers the vehicle, and a myoelectric potential of one of the right and left masseter muscles of the driver is constantly measured (step S100).

In the myoelectric potential measurement, the sensor unit 12 acquires a myoelectric potential of one of the masseter muscles while steering, and amplifies it using the amplifier 16, and time-series data of the myoelectric potential is output to the myoelectric-potential data processing part 22 of the processor unit 20.

The myoelectric-potential data processing part 22 rectifies and smoothes the time-series data of the myoelectric potential of the masseter muscle that is obtained to thereby generate a myoelectric potential waveform. Then, the myoelectric-potential data processing part calculates the myoelectric potential intensity in a predetermined time region corresponding to a predetermined running section, from the myoelectric potential waveform (step S102).

Specifically, the time-series data of the myoelectric potential of the masseter muscle that is measured by the sensor unit 12 and amplified by the amplifier 16, is rectified to form a signal waveform whose values are all equal to or higher than 0, and the signal waveform is smoothed by a filtering process of a low-pass filter to provide a smooth myoelectric potential waveform containing a little noise. The myoelectric-potential data processing part 22, thereafter, calculates an RMS value (effective value), as a myoelectric potential intensity, of the myoelectric potential waveform in a given time region corresponding to a running section, from the myoelectric potential waveform.

During driving, time-series data on lateral acceleration as the external force physical quantity is measured (step S104).

The lateral acceleration of the vehicle is measured by an acceleration pickup attached to the console of the vehicle, and recorded by a recorder mounted on the vehicle, such as data logger.

In the case of measuring the myoelectric potential of the muscle which is exercised for holding the posture of the driver, the sensor unit 12 and the amplifier 16 shown in FIG. 2, which are used when the myoelectric potential of the masseter muscle are measured, will be used. Then the electrodes 12a and 12b of the sensor unit 12 will be stuck to a surface of a skin covering the muscle to be measured, and a myoelectric potential will be measured and recorded by a recorder mounted on the vehicle, such as a logger.

Then, the time-series data of the measured external force physical quantity is supplied to the external-force level judging part 24 of the evaluating device 10, and a level of an external force is obtained in the external-force level judging part 24.

Specifically, the time-series data of the lateral acceleration as the measured external force physical quantity, like the time-series data of the myoelectric potential already stated, is rectified and smoothed to generate an external force physical quantity waveform. An RMS value (effective value) of the external force physical quantity waveform in a predetermined time region is calculated, and the resultant is set as an external force level (step S106).

Next, the normalizing part 26 normalizes the myoelectric potential intensity in the predetermined time region which is obtained in step S102 by using the external force physical quantity intensity (external force level) in the predetermined region which is obtained in step S106, and the normalized myoelectric potential intensity is output to the evaluating part 28 (step S108). The evaluating part 28 compares the normalized myoelectric potential intensity with set values of respective stages previously set for stagewise evaluation on levels of stress of the driver at steering to thereby evaluate the level of stress of the driver while steering, and the evaluation result is sent to the monitor 34 (step S100).

The first embodiment of the stress-at-steering evaluating method according to the present invention is as described above.

The masseter muscles of the driver act also to hold the posture of the driver against an external force acting on the driver's head. Accordingly, myoelectric potentials of the masseter muscles measured contain the myoelectric potentials resulting from the activities of the masseter muscles for holding the posture. In the first embodiment of the present invention, the myoelectric potential intensity normalized by the external force level (external force physical quantity intensity) is used. Therefore, the myoelectric potential intensity of the masseter muscle, which is generated as the result of the "teeth clenching" due to the stress, can be evaluated under less influence of the activities of the masseter muscles for holding the posture.

During the "teeth clenching" due to the stress, the right and left masseter muscles concurrently act. Therefore, when stress is placed on the driver, the myoelectric potentials of both masseter muscles increase. In contrast, when the masseter muscles act to hold the posture, the right and left masseter muscles independently act. Accordingly, only the myoelectric potential of one of the right and left masseter muscles increases as illustrated by the sternocleidomastoid in FIGS. 3A and 3B. For this reason, by using the simultaneous contraction intensity, the myoelectric potential intensity of the masseter muscles, which is generated as the result of the "teeth clenching" due to the stress, can be evaluated under less influence of the activities of the masseter muscle in holding the posture.

Figure 6:
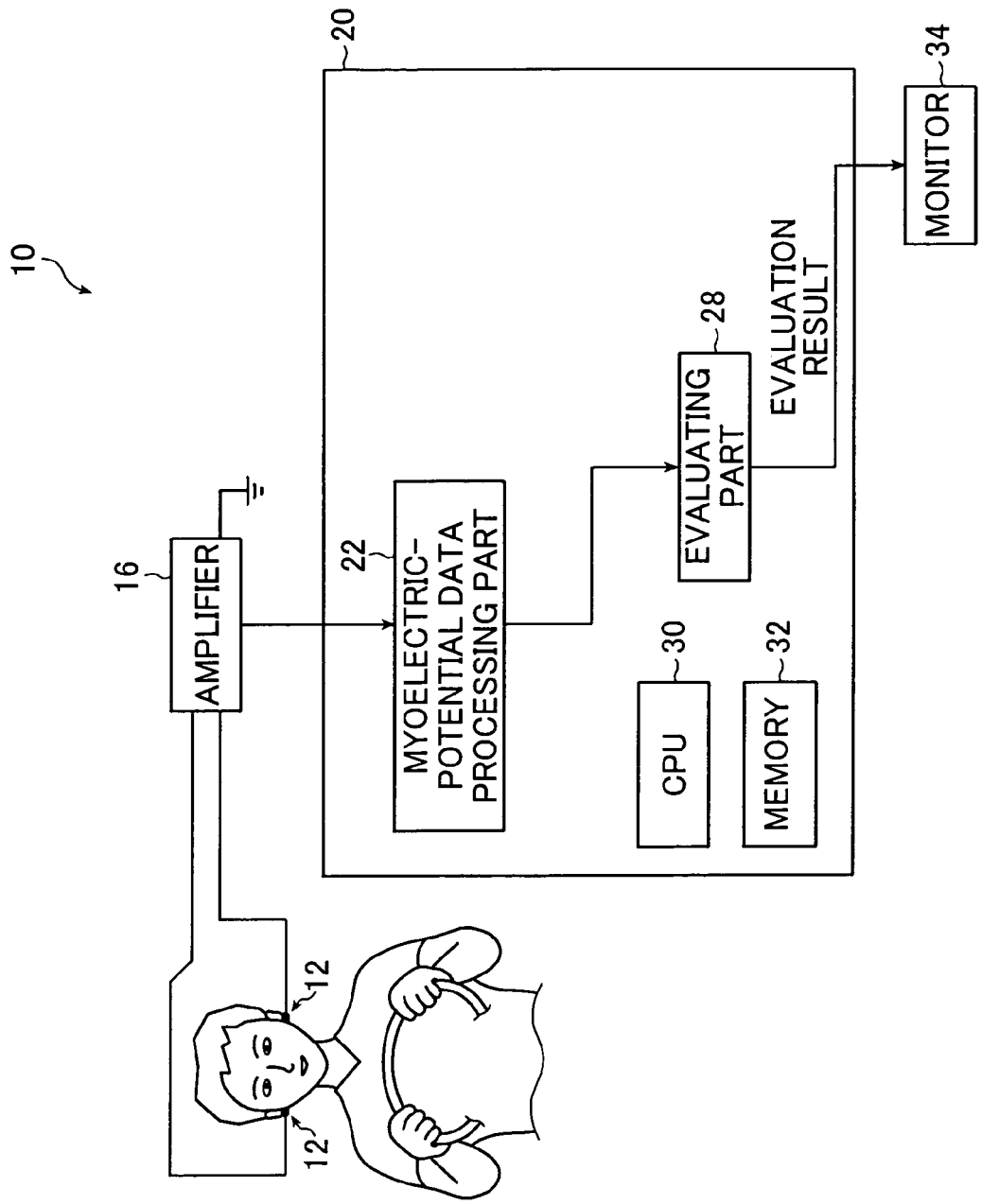
FIG. 6 is a diagram, in block and schematic form, showing a steering stress evaluating device 10 of a second embodiment of the present invention.
Figure 7:
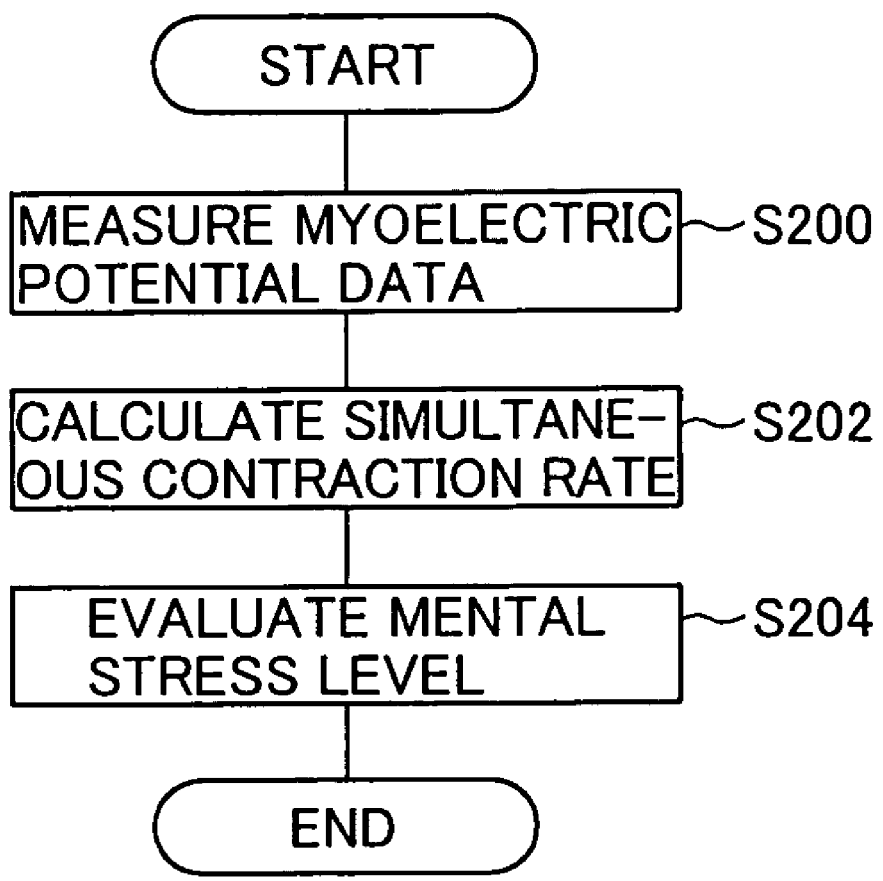
FIG. 7 is a flow chart for explaining a second embodiment of a method for evaluating a stress of a driver at steering, which is carried out by using the steering stress evaluating device 10.

A second embodiment of a method for evaluating a stress of a driver during driving will be described. FIG. 6 is a diagram, in block and schematic form, showing a steering stress evaluating device 10 of the second embodiment of the present invention. FIG. 7 is a flow chart for explaining a second embodiment of a method for evaluating the stress of a driver while steering, which is carried out by using the steering stress evaluating device 10. In the second embodiment of the stress-at-steering evaluating method, time-series data of the myoelectric potentials of the right and left masseter muscles of the driver as he/she steers the vehicle are measured, and the simultaneous contraction intensity in a predetermined time region at steering is obtained, and stress placed on the driver at steering is evaluated by using the simultaneous contraction intensity.

In the second embodiment of the stress-at-steering evaluating method, as shown in FIGS. 6 and 7 a plurality of sensor units 12 are attached, as in the first embodiment, to the driver as a subject. In this state, the driver starts driving and steering of a vehicle, a myoelectric potentials of the right and left masseter muscles of the driver are constantly measured, and time-series data of the myoelectric potentials of the masseter muscles when the driver-steers the vehicle is acquired by the sensor units 12 (step S200).

In this myoelectric potential measurement, a plurality of sensor units 12 acquires the myoelectric potentials of the right and left masseter muscles generated when the driver steers the vehicle, the amplifier 16 amplifies the myoelectric potentials, and time-series data of the myoelectric potentials of the right and left masseter muscles are output to the myoelectric-potential data processing part 22 of the processor unit 20.

The myoelectric-potential data processing part 22 rectifies and smoothes the time-series data of the myoelectric potentials of the right and left masseter muscles to generate myoelectric potential waveforms. The myoelectric-potential data processing part 22 then calculates from the myoelectric potential waveforms a geometric average of the myoelectric potentials of the right and left masseter muscles at the same time point to generate the simultaneous contraction waveform, and calculates the simultaneous contraction intensity as an RMS value of the simultaneous contraction waveform at a fixed time interval. (step S202).

In the present invention, the simultaneous contraction intensity in a predetermined time region may be calculated in such a manner that, by using a waveform, which is generated by selecting the smaller of the two values of the myoelectric potentials of the right and left masseter muscles at the same time point, for the simultaneous contraction waveform, an RMS value of the simultaneous contraction waveform generated is calculated. A specific example of the method of generating the simultaneous contraction waveform and calculating the simultaneous contraction intensity is described in Japanese Patent Application No. 2002-212683, filed by the applicant of the present patent application. In this patent application, a synchronous contraction waveform (simultaneous contraction waveform) based on the right and left deltoid muscles of a subject is generated, and the comfort at work which is experienced by the worker is evaluated based on intensity information (simultaneous contraction intensity) of the synchronous contraction waveform, the intensity information is calculated from the synchronous contraction waveform. Also in the present invention, the myoelectric potentials of the masseter muscles may be processed in a manner similar to the processing of the myoelectric potentials of the deltoid muscles in the invention of the above patent application.

In the second embodiment, the calculated simultaneous contraction intensity is output to the evaluating part 28 without undergoing any processing in the normalizing part 26. In the evaluating part, it is compared with set values of respective stages previously set for stagewise evaluation on levels of stress of the driver while steering to thereby evaluate a level of stress of the driver while steering (step S204).

The second embodiment of the present invention can evaluate intensities of myoelectric potentials generated when both the right and left masseter muscles simultaneously act as the result of the "teeth clenching" of the driver, by using the simultaneous contraction intensity. Therefore, it is possible to evaluate the stress of a driver at work under less influence of the activities of the muscles for holding the posture, without normalizing the external force acting on the head by the external force level, as in the first embodiment.

However, the intensity information on the myoelectric potentials generated when the right and left muscles independently act is not perfectly removed from the simultaneous contraction intensity. Accordingly, to more accurately obtain the myoelectric potential intensity caused by the "teeth clenching" resulting from the stress, it is preferable to normalize the simultaneous contraction intensity by the external force level.

A subject's stress can be evaluated more accurately by normalizing the simultaneous contraction intensity by the level of the external force acting on the head. A stress-at-steering evaluating method based on such a technique will be described as a third embodiment of the present invention. Such a stress evaluating method according to the third embodiment will be described hereunder.

Figure 8:
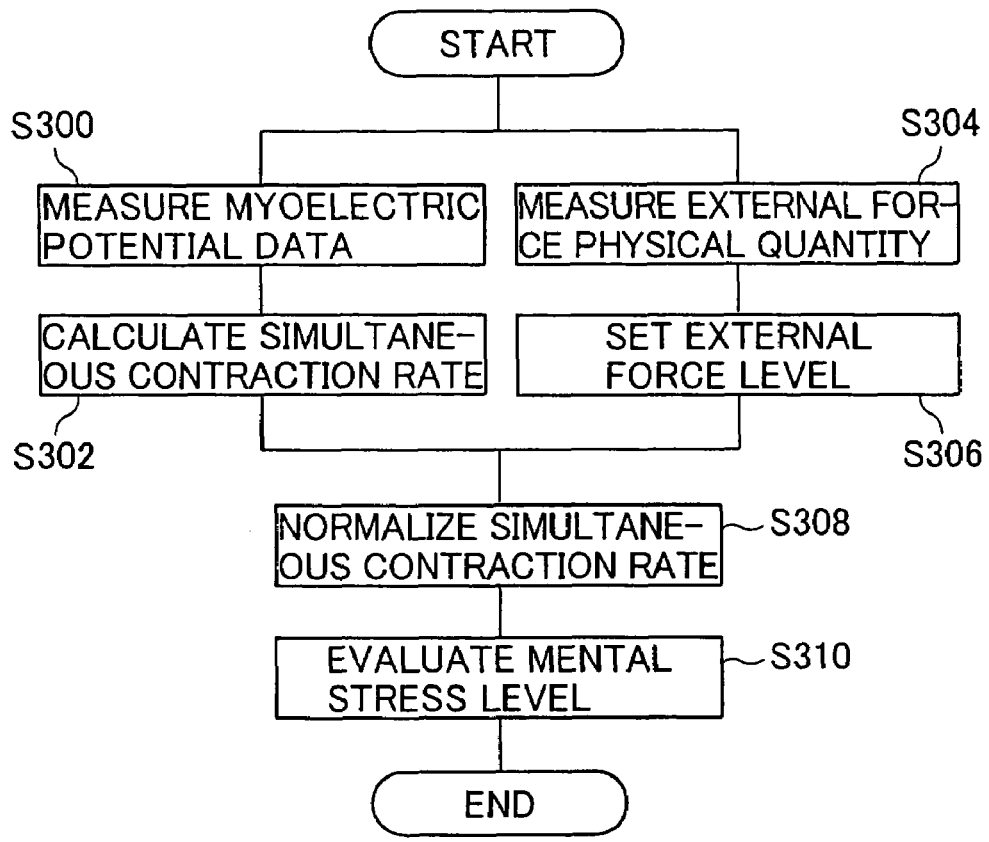
FIG. 8 is a flow chart for explaining a third embodiment of a method for evaluating a mental stress during steering of a vehicle, which is performed by using the steering stress evaluating device 10.

FIG. 8 is a flow chart for explaining the third embodiment of a method for evaluating a mental stress during steering of a vehicle, which is performed by using the evaluating device 10 shown in FIG. 1.

First, a driver drives a vehicle, in the same manner as in step S200 in the second embodiment. Time-series myoelectric potential data of the right and left masseter muscles of a driver who is driving the vehicle are measured (step S300). In the same manner as in step S202 in the second embodiment, a simultaneous contraction intensity of the right and left masseter muscles is calculated from the time-series myoelectric potential data of the right and left masseter muscles (step S302).

During driving, time-series data of an external force physical quantity is measured (step S304) in the same manner as in step S104 of the first embodiment, and a level of an external force is set based on the time-series data (step S306) as in step S106 of the first embodiment. Subsequently, in the normalizing part 26, the simultaneous contraction intensity calculated in step S302 is divided by the external force level set in step S306 to be normalized (step S308). The stress of the driver at work is evaluated by using the normalized simultaneous contraction intensity (step S310) as in step S204 of the second embodiment. In this way, the influence of the external force when the subject is doing work is further removed, and in this condition, myoelectric potentials of the masseter muscles of the subject caused by the stress can be evaluated. Hence, the stress of the subject can be evaluated more precisely.

The data processing method in each of the first, second, and third embodiments of the invention may be modified as follows. A first normalizing process is carried out as follows. In the process, one or more waveforms obtained by rectifying time-series data of the measured myoelectric potentials are normalized by using a maximum myoelectric potential or potentials that are previously measured and recorded to thereby compute indices. The normalized myoelectric potential waveform or waveforms which have been obtained by the first normalizing process are generated. The stress of the subject is evaluated using the normalized myoelectric potential waveform or waveforms.

The influence of electric resistance of the electrodes 12a and 12b, which varies every time the sensor unit 12 is stuck to the subject, is lessened by normalizing the time-series data of the myoelectric potential by using the maximum myoelectric potential (first normalizing process). When the electrodes 12a and 12b are applied multiple times, to evaluate the stress of the subject more precisely, it is preferable to use the normalized myoelectric potential waveform.

In the first, second, and third embodiments of the invention, the myoelectric potential intensity or the simultaneous contraction intensity in a predetermined time region is calculated from time-series myoelectric potential data of one or both of the right and left masseter muscles.

In the present invention, a myoelectric potential intensity or a simultaneous contraction intensity may be calculated in a first time region. The first time region is obtained by removing a second time region from a given time region. The second time region is a time region when the subject exercises the masseter muscles in no relation to the objective work, such as mastication or conversation, which is recognized by using recorded motion picture data or recorded voice data of the subject at work.

In a case where the subject may exercise the masseter muscles such as for mastication or conversation, a stress placed on the subject during the objective work can be very precisely evaluated by calculating a myoelectric potential intensity or a simultaneous contraction intensity in the above mentioned first time region, excluding the time region when the subject exercises the masseter muscles, such as mastication or conversation, in no relation to the objective work.

EXAMPLE

Comparison tests were conducted by using the steering stress evaluating device 10 according to the present invention. In the tests, stress evaluations were performed as follows. The stress-at-driving evaluating method of the first embodiment of the present invention was used for the evaluation. Vehicles having different vehicle characteristics were used. Stress of a driver was measured for each vehicle characteristic when he/she steers the vehicles. The test results will be presented below.

Figure 9:
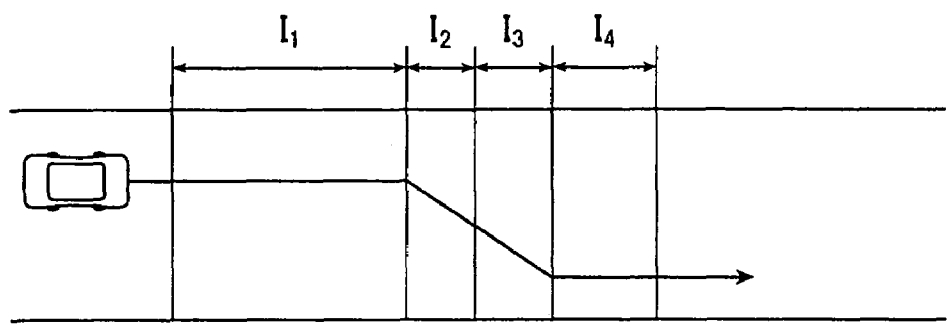
FIG. 9 is a schematic diagram showing a traveling path along which the vehicle runs in stress comparison tests conducted for each vehicle characteristic when a driver steers the vehicle.

FIG. 9 schematically illustrates a vehicle traveling path in this example. To evaluate the stress, in this example, a lane change section was divided into four subsections of approaching ($I_1$), steering-start ($I_2$), turning ($I_3$), and corrective steering ($I_4$). Each driver as a subject was instructed to drive the vehicle along the traveling path at constant speed.

Five vehicles, S1 to S5, having different vehicle characteristics were used. The different vehicle characteristics were differences in the kind of mounted tires and differences in the combination of the kind of mounted tires, i.e., which kind of tires are mounted on the front wheels and which kind of tires are mounted on the rear wheels.

In this example, two drivers, D1 and D2, each drove the five vehicles having different specifications five times along the traveling path shown in FIG. 9. Time-series myoelectric potential data of the masseter muscles and time-series data of lateral acceleration as external force physical quantity data were measured for each vehicle running. A myoelectric potential intensity and an external force physical quantity intensity were calculated from the time-series myoelectric potential data and time-series data of lateral acceleration, which were obtained by the measurement, and the myoelectric potential intensity was normalized i.e., divided by the external force physical quantity intensity.

Figure 10A:
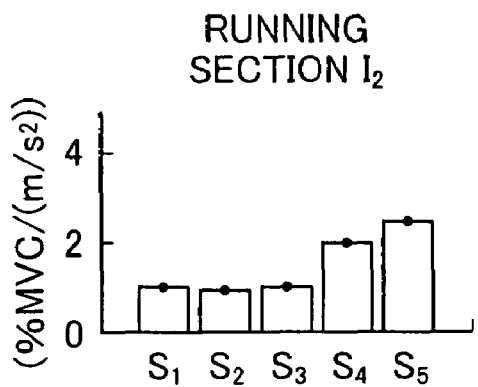
FIGS. 10A and 10B are graphs showing values of normalized myoelectric potential intensities obtained when a driver D1 steers vehicles having different vehicle characteristics in predetermined subsections.
Figure 10B:
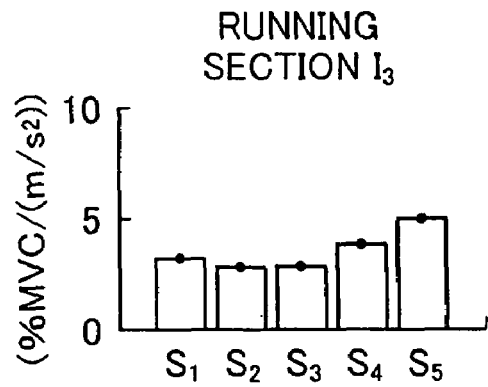

FIGS. 10A and 10B are graphs showing values of normalized myoelectric potential intensities obtained when the driver D1 steers the vehicles having vehicle characteristics defined by specifications S1 to S5 in the subsections $I_2$ and $I_3$. The graph of FIG. 10A and the graph of FIG. 10B show the values of the normalized myoelectric potential intensities for the subsection $I_2$ and the subsection $I_3$, respectively.

Figure 11A:
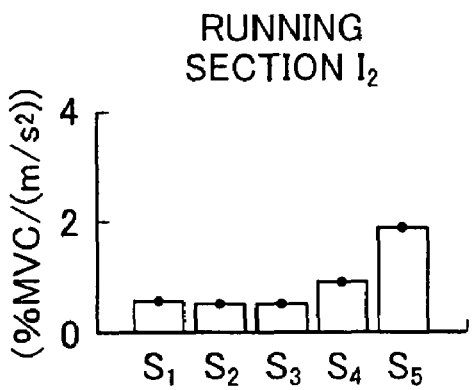
FIGS. 11A and 11B are graphs showing values of normalized myoelectric potential intensities obtained when a driver D2 steers vehicles having different vehicle characteristics in predetermined subsections.
Figure 11B:
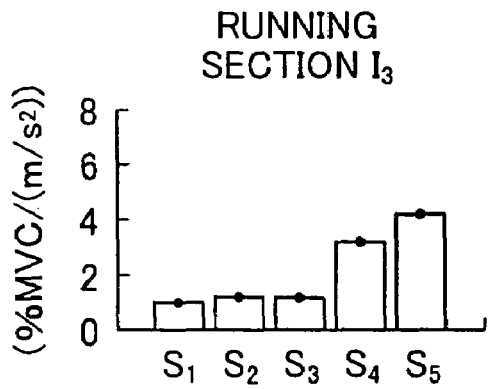

FIGS. 11A and 11B are graphs showing values of normalized myoelectric potential intensities obtained when a driver D2 steers vehicles having vehicle characteristics defined by specifications S1 to S5 in the subsections $I_2$ and $I_3$, respectively. The graph of FIG. 11A and the graph of FIG. 11B show the values of the normalized myoelectric potential intensities for the subsection $I_2$ and the subsection $I_3$, respectively.

In the subsections $I_2$ and $I_3$, the driver steers the steering wheel to actively change an advancing direction of the vehicle. In those subsections, the steering operation is difficult and a stress of the driver is large as compared with those in the subsections $I_1$ and $I_4$ where the vehicle travels straight ahead.

As seen from FIGS. 10A and 10B and 11A and 11B, the normalized myoelectric potential intensity values obtained when the driver steers the vehicle of the specifications S4 and S5 are larger than those when he/she drives the vehicles of other specifications. This is true for both a case where the steering wheel is turned to the right (subsection $I_2$) and a case where it is turned to the left (subsection $I_3$). From this fact, it is judged that a large stress is placed on the driver who drives the vehicles of the specifications S4 and S5.

Samples of sensory values of the drivers as subjects are presented as comparison examples.

Figures 12A, 12B:
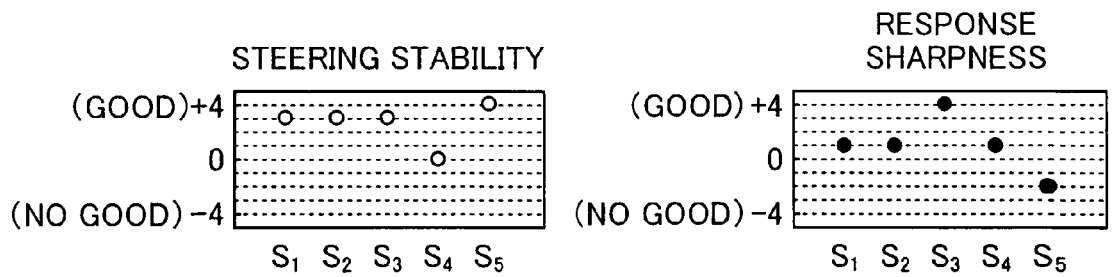
FIGS. 12A and 12B are graphs showing sensory values of steering stability and response sharpness obtained when the driver D1 steers vehicles having different vehicle characteristics in predetermined subsections.
Figures 13A, 13B:
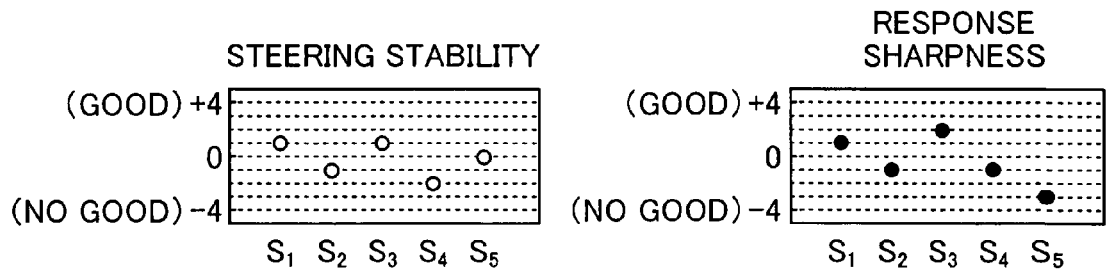
FIGS. 13A and 13B are graphs showing sensory values of steering stability and response sharpness steering stability obtained when the driver D2 steers vehicles having different vehicle characteristics in the predetermined subsections.

FIGS. 12A and 13A are graphs showing sensory values of maneuvering stability (steering stability) obtained when a driver drives vehicles having the respective vehicle characteristics in the subsections $I_1$ to $I_4$. From the graphs, both the drivers D1 and D2 answered that the maneuvering stability (steering stability) was the poorest with the vehicle of the specification S4. The result coincides with the results shown in FIGS. 10A and 10B and 11A and 11B that the drivers suffer from large stress when they drive the vehicle of the specification S4.

FIGS. 12B and 13B are graphs showing sensory values of vehicle response sharpness obtained when the driver drives vehicles having the respective specifications. From the graphs, both the drivers D1 and D2 answered that the response sharpness was the poorest with the vehicle of the specification S5. The result coincides with the results shown in FIGS. 10A and 10B and 11A and 11B that the drivers suffer from large stress when they drive the vehicle of the specification S5.

From the test results described above, it is understood that the level of stress of the driver during steering of a vehicle is properly evaluated by using the normalized myoelectric potential intensity, in which the normalized myoelectric potential intensity is obtained by dividing the myoelectric potential intensity of the masseter muscle at vehicle steering by an external force physical quantity intensity.

In the example described above, a stress placed on the driver when he/she drives the vehicle was described. However, the objective work for which the level of the stress is evaluated is not limited to driving of a vehicle. Objective work may be any work involving activities of muscles other than the masseter muscle.

While the stress-at-work evaluating device and the stress-at-work evaluating method have been described in detail, it should be understood that the present invention is not limited to the above examples various improvements and modifications may be made without departing from the gist of the invention.

We claim:

1. A stress-at-work evaluating method for evaluating stress of a subject at work based on measuring the activities of one of the right and the left masseter muscles, the work including exercise of the subject's arms or feet, wherein the stress-at-work evaluating method comprises:
    a myoelectric potential measurement step of sensing and amplifying a myoelectric potential of one of the right and the left masseter muscles, the potential being generated through the activities of one of the right and the left masseter muscles at work;
    a processing step of processing time-series data of the measured myoelectric potential of the one of the right and the left masseter muscles and calculating the intensity information on myoelectric potential of the one of the right and the left masseter muscles;
    a judging step of judging the level of an external force acting on the subject's head, the external force measured simultaneously with the myoelectric potential; and
    an evaluating step of evaluating the level of stress of the subject at work, wherein the level of stress is obtained by dividing the calculated intensity of the myoelectric potential by the judged level of the external force.

2. The stress-at-work evaluating method according to claim 1, wherein the judging step of judging the level of the external force uses measured external force data of a measurement time region, which is identical to the measurement time region used in the myoelectric potential measurement step.

3. A stress-at-work evaluating device for evaluating stress of a subject at work based on measuring the activities of one of the right and the left masseter muscles, the work including exercise of the subject's arms or feet, wherein the stress-at-work evaluating device comprises:
    a sensor unit for sensing a myoelectric potential of one of the right and the left masseter muscles, the myoelectric potential being generated through the activities of one of the right and the left masseter muscles at work;
    an amplifier for amplifying the myoelectric potential sensed by the sensor unit;
    a myoelectric-potential data processing part for processing time-series data of the amplified myoelectric potential of the one of the right and the left masseter muscles, to thereby calculate the intensity of the myoelectric potential of the one of the right and the left masseter muscles;
    an external-force level judging part for judging the level of an external force acting on a portion of the head of the subject at work, the external force measured simultaneously with the myoelectric potential; and
    an evaluating part for evaluating the level of stress of the subject at work, wherein the level of stress is obtained by dividing the calculated intensity of the myoelectric potential by the judged level of external force.

4. The stress-at-work evaluating device according to claim 3, wherein the external-force level judging part judges the level of the external force acting on the portion of the subject's head based on the intensity of the myoelectric potential of at least one of the muscles that maintains the posture of the portion of the subject's head.

5. The stress-at-work evaluating device according to claim 3, wherein the subject works to move a predetermined object thereby causing the external force acting on the portion of the subject's head and wherein the external-force level judging part judges the level of the external force acting on the portion of the subject's head by using at least one physical quantity representing the movement of the predetermined object, the movement caused by the subject's work.

6. The stress-at-work evaluating device according to claim 5, wherein the work is a steering operation which is done by the subject.

7. The stress-at-work evaluating device according to claim 3, wherein the evaluating part further evaluates the stress of the subject at work by comparing the level of stress with predetermined values.

8. The stress-at-work evaluating device according to claim 3, wherein the external-force level judging part judges the level of the external force from measured external force data of a measurement time region, which is identical to the measurement time region used by the myoelectric-potential data processing part to process the myoelectric potential.

* * * * *

UNITED STATES PATENT AND TRADEMARK OFFICE
CERTIFICATE OF CORRECTION

PATENT NO.         : 7,467,010 B2                                             Page 1 of 1
APPLICATION NO.    : 10/942041
DATED              : December 16, 2008
INVENTOR(S)        : Akira Kuramori et al.

It is certified that error appears in the above-identified patent and that said Letters Patent is hereby corrected as shown below:

On the Title Page, Item (73) "Yokohama Rubber Co., Ltd.," should read -- The Yokohama Rubber Co., Ltd., --.

Signed and Sealed this

Seventh Day of April, 2009

JOHN DOLL
*Acting Director of the United States Patent and Trademark Office*